United States Patent [19]

Mikhail

[11] Patent Number: 5,314,493
[45] Date of Patent: May 24, 1994

[54] FEMORAL HIP JOINT PROSTHESIS

[76] Inventor: W. E. Michael Mikhail, 4203 Shamley Green, Toledo, Ohio 43623

[21] Appl. No.: 942,993

[22] Filed: Sep. 10, 1992

[51] Int. Cl.$^5$ ............................................. A61F 2/30
[52] U.S. Cl. ......................................... 623/23; 623/18
[58] Field of Search .................. 623/16, 18, 19, 20, 623/22, 23

[56] References Cited

U.S. PATENT DOCUMENTS

| 3,924,274 | 12/1975 | Heimke et al. | 623/18 |
| 4,936,859 | 6/1990 | Morscher et al. | 623/16 |
| 5,078,746 | 7/1992 | Garner | 623/16 |
| 5,080,680 | 1/1992 | Mikhail et al. | 623/23 |
| 5,092,892 | 3/1992 | Ashby | 623/16 |
| 5,197,990 | 3/1993 | Lawes et al. | |

FOREIGN PATENT DOCUMENTS 9105872 7/1991 Fed. Rep. of Germany ........ 623/23

Primary Examiner—David Isabella
Attorney, Agent, or Firm—Emch, Schaffer, Schaub & Porcello Co.

[57] ABSTRACT

A femoral hip joint prosthesis includes a metal component having a double tapered stem and a preapplied cement mantle with an integral centralizer.

12 Claims, 4 Drawing Sheets

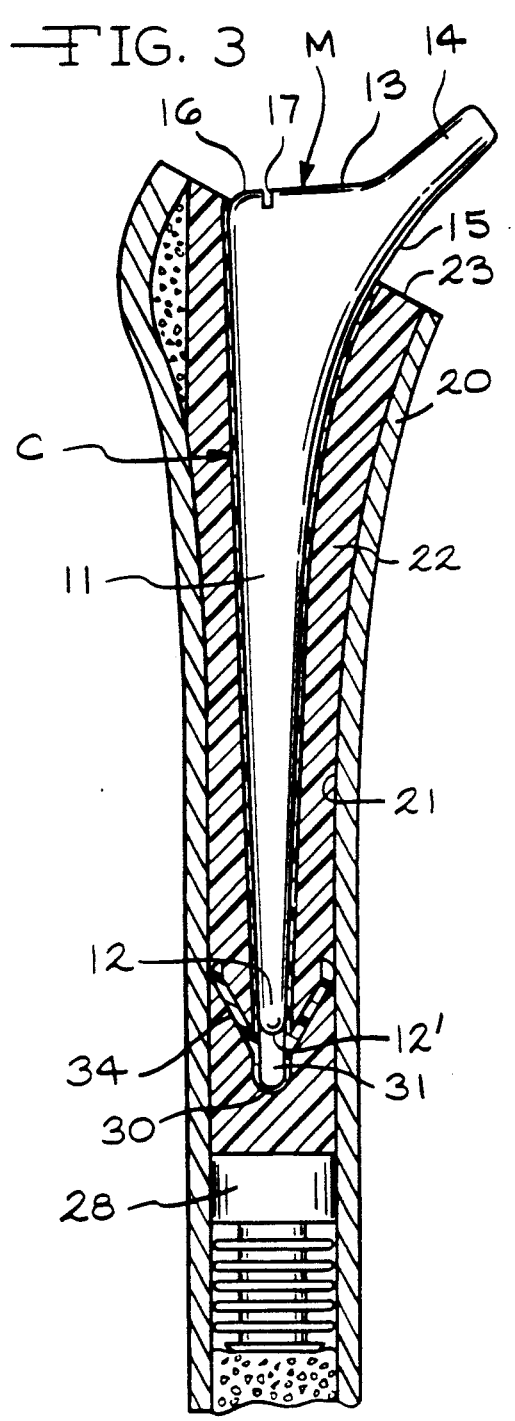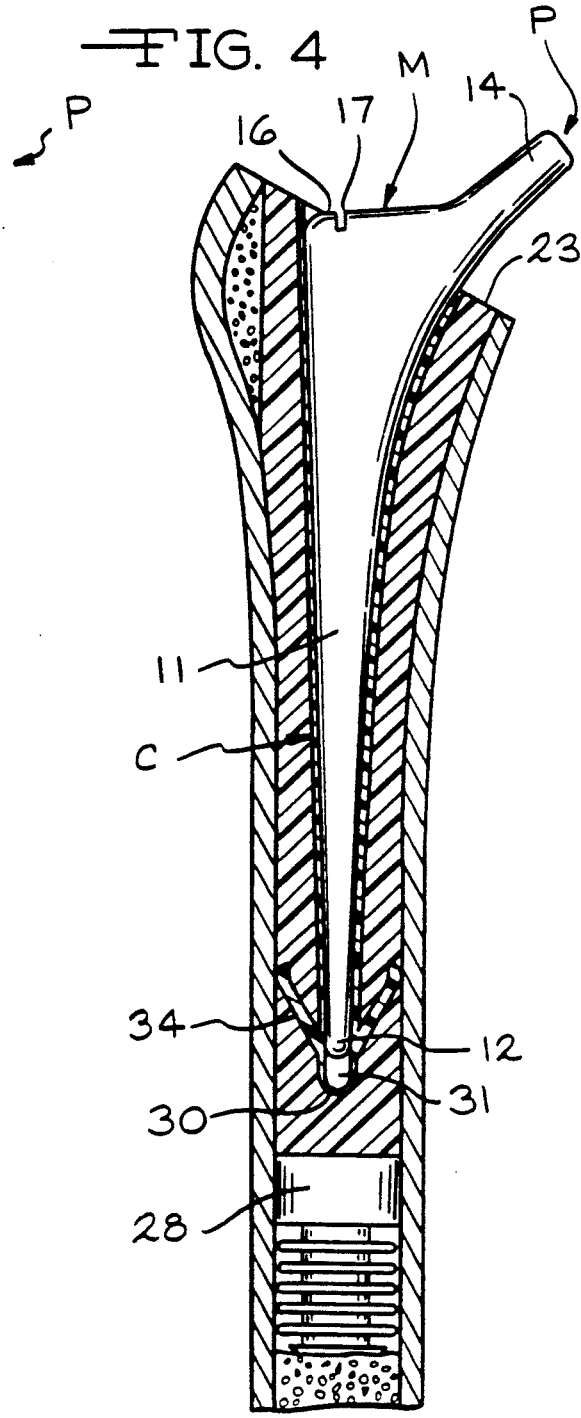

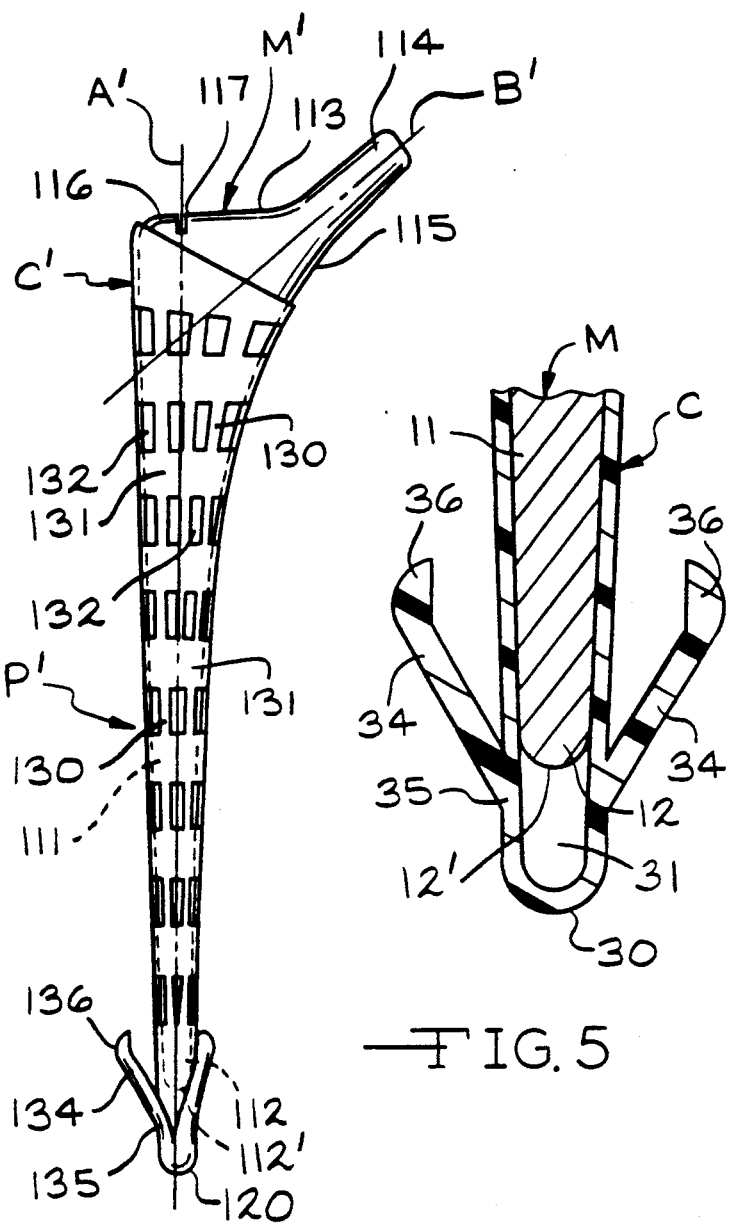

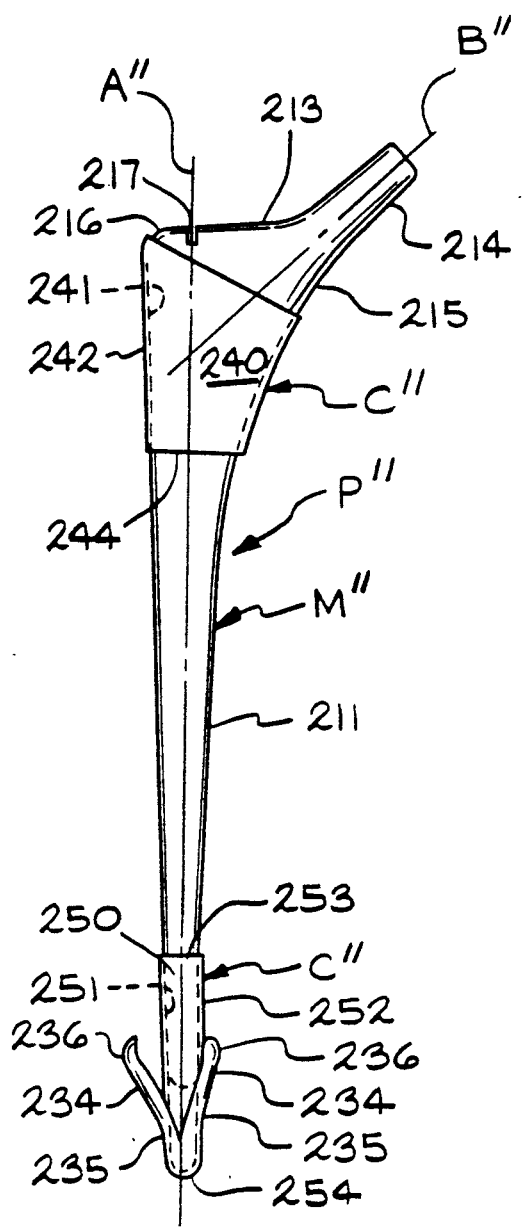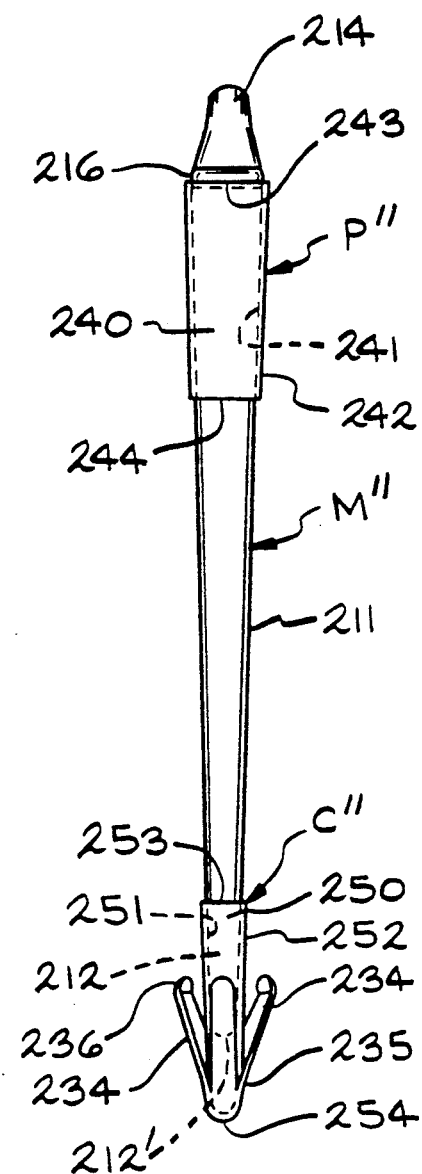
FIG. 8
FIG. 9

FEMORAL HIP JOINT PROSTHESIS

BACKGROUND ART

The present invention relates to a hip joint prosthesis and more particularly to a femoral component of such prosthesis. U.S. Pat. No. 5,080,680, of which I am a co-inventor, discloses a femoral stem prosthesis with a preapplied cement mantle. A continuation-in-part application of such patent, namely, application Ser. No. 07/673,367, filed Mar. 22, 1991, discloses another embodiment in which the preapplied cement mantle has a series of interstices or openings in the preapplied cement mantle.

As disclosed in the above patent and continuation-in-part application, each of such prostheses is implanted in the intramedullary canal of the femur of a patient, normally with its distal end positioned in a centralizer which assures proper positioning of such distal end in the central area of the intramedullary canal. As is well-known in the field of implanting femoral prostheses, bone cement such as polymethylmethacrylate (PMMA) is normally used to fix the femoral stem prostheses in position. With each of the femoral stem prostheses disclosed in U.S. Pat. No. 5,080,680 and application Ser. No. 07/673,367, filed Mar. 22, 1991, (both of which are incorporated herein by reference) there is a gap between the end of the preapplied cement mantle and the upper end of the centralizer. There is a possibility that, upon implantation of either of such prostheses, the new bone cement will not completely fill the gap and will leave a portion of the stem of the metal component immediately above the centralizer uncontacted by bone cement. The presence of any such uncontacted area could lead to osteolysis and eventual loosening and failure of the implanted prosthesis.

SUMMARY OF THE INVENTION

Under the present invention, there is provided a femoral stem prosthesis comprising a metal component having a preapplied cement mantle with an integral centralizer at its distal end. The femoral stem prosthesis is preferably produced of an alloy of cobalt chrome molybdenum and has a highly polished finish in order to permit the prosthesis to subside within the preapplied cement mantle over time. The metal component is preferably of the type disclosed in U.S. patent application Ser. No. 07/804,623, filed Dec. 6, 1991, of which I am a co-inventor (incorporated herein by reference). The distal end of the stem of the metal component is spaced from the lower end of the pocket of the integral centralizer portion of the preapplied cement mantle in order to leave a space into which such distal end may move as a result of any such subsidence. Under one embodiment the preapplied cement mantel has a uniform tapered wall covering the entire surface of the stem from the distal end (except for the tip) to an area near the shoulder while under another embodiment it has an intermittent coating with interstices.

It is an object of the present invention to provide a femoral hip joint prosthesis with a preapplied cement mantle which will not loosen but, rather, will self-tighten even though the cement mantle creeps or expands fractionally over a period of time and will be centralized upon implantation in the intramedullary canal of a femur.

It is yet another object of the present invention to provide a femoral hip joint prosthesis having a preapplied cement mantle with integral centralizer which becomes joined with and an integral part of additional cement placed in the intramedullary canal upon implantation. Upon subsidence of the metal component within the cement mantle as the cement creeps, the stem remains at all times in snug interfacial contact with the cement thus imparting in the stem area the reliable compressive forces against the cement which is micro-interlocked with the bony surface.

It is another object of the present invention to provide a femoral hip joint prosthesis having a preapplied cement mantle implanted in a femoral canal having additional cement which is self-centralizing and yet permits subsidence within the cement mantle without disrupting the micro-interlocking and thus preserving the cement-bone interface.

BRIEF DESCRIPTION OF THE DRAWINGS

FIG. 3 is a sectional view showing the femoral hip joint prosthesis of the present invention immediately after implanting in a patient.

FIG. 4 is a view similar to FIG. 3 showing the femoral hip joint prosthesis after being implanted for a number of years and showing, greatly exaggerated, the effects of subsidence.

FIG. 5 is an enlarged fragmentary sectional view of the distal end of the femoral hip joint prosthesis of the present invention.

FIG. 6 is a front elevational view of another embodiment of the femoral hip joint prosthesis according to the present invention having an intermittent preapplied cement mantle.

FIG. 7 is an end view of the femoral hip joint prosthesis of FIG. 6.

FIG. 8 is a front elevational view of yet another embodiment of the femoral hip joint prosthesis of the present invention.

FIG. 9 is an end view of the femoral hip joint prosthesis of FIG. 8.

BEST MODE OF CARRYING OUT INVENTION

Figure 1:
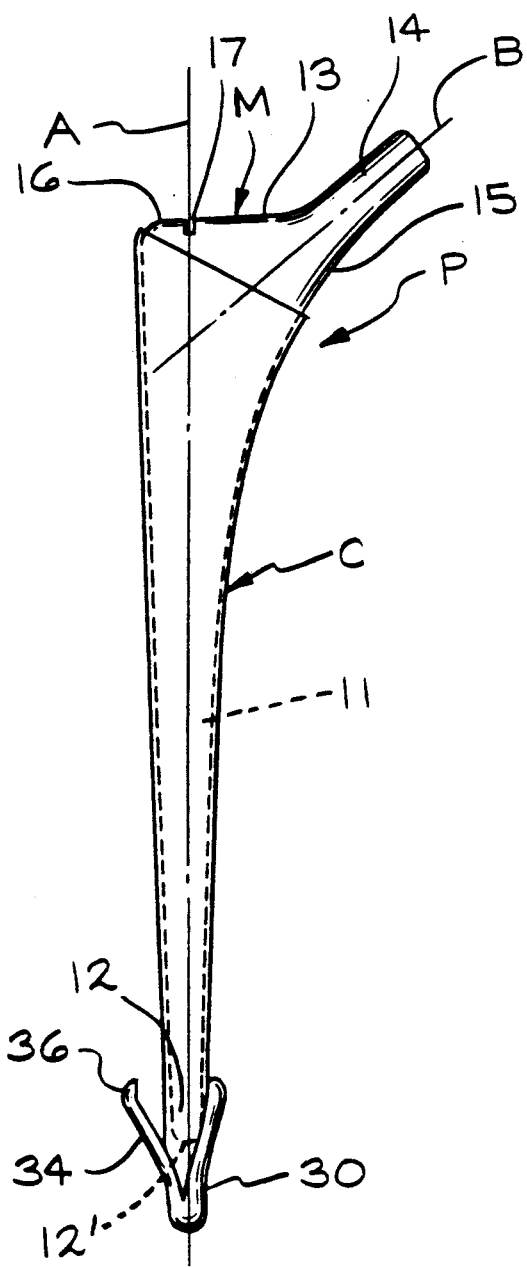
FIG. 1 is a front elevational view of the femoral hip joint prosthesis according to the present invention.

Referring now to FIGS. 1–5, there is shown a femoral hip joint prosthesis P comprising a metal component M and a preapplied cement mantle C with integral centralizer. The metal component M includes a stem 11 which is convergently tapered toward a distal end 12 and extending along a first axis of symmetry A to an area of juncture with a neck portion 13 lying on a second axis of symmetry B. The distal end 12 terminates in a tip 12'. Extending from the neck portion 13 is a frustoconically-shaped Morse Taper Neck 14 to which may be attached a spherically-shaped Morse Taper Head. As is clear from FIG. 1, no collar is provided in the femoral hip prosthesis, but rather the portion of the metal component M joining the stem 11 to the neck 13 follows a smooth arcuate contour in the area 15 of the included angle between the respective axes of symmetry A and B. The portion of the metal component M opposite the smooth arcuate portion 15, namely, that portion on the outside of the angle between the two axes of symmetry A and B, has an enlarged shoulder 16 in which is formed a dimple or recess 17 for driving the prosthesis into the femur. As can be seen, the dimple 17 is located on the first axis of symmetry A.

Figure 2:
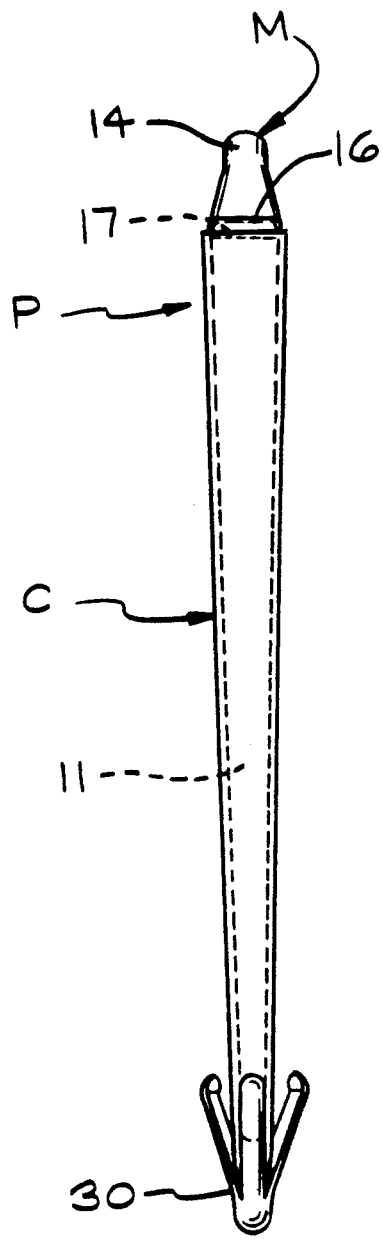
FIG. 2 is an end view of such femoral hip joint prosthesis.

As can be seen in FIGS. 1–3, the stem 11 is tapered in both directions. As pointed out in United Kingdom Patent Specification 1,409,054, such double tapering enhances the extrusion of cement caused by penetration of the prosthesis P thereinto during fixation.

The femoral hip joint prosthesis further includes a preapplied cement mantle C of PMMA or other commercially available bone cement. The preapplied cement mantle C encapsulates the entire stem 11 from an area beyond the distal end 12 but not contacting the tip 12' up to the area of the smooth arcuate portion 15 and the beginning of the enlarged shoulder 16. Thus, the preapplied cement mantle C extends to a closed end 30, the interior surface of which is spaced from the tip 12' and defines a pocket 31 within which the distal end 12 may move upon subsidence of the stem 11 within the cement mantle C. The distance between the distal end 12 and the interior surface of the closed end 30 of the preapplied cement mantle C should be in the range of 5 to 10 millimeters (mm).

A plurality of wings 34, preferably three or four in number, extend upwardly in a direction away from the closed end 30 and outwardly away from the axis A. The wings 34 extend in cantilever fashion from a lower end 35 integral with the wall of the preapplied cement mantle C in a location somewhat upwardly from the closed end 30 and generally aligned with the distal end 12 of the metal component M to an upper end 36 spaced from the wall of the preapplied cement mantle C. The wings 34 are resilient and their upper ends 36, prior to insertion in a femoral intramedullary canal are disposed approximately 3 to 5 millimeters (mm) from the wall of the preapplied cement mantle. Thus, the outer extent in which the upper ends 36 of the wings 34 will contact the interior wall of the prepared intramedullary canal prior to reaching its fully inserted position and will be biased inwardly thereby centralizing the position of the distal end of the prosthesis P in the intramedullary canal.

Preferably, the preapplied cement mantle C has a substantially uniform thickness with the thickness being at least seven-tenths of a millimeter (0.7 mm) and no thicker than about two millimeters (2 mm). Such preapplied cement mantle C is allowed to become fully set so that the femoral hip joint prosthesis P including such preapplied cement mantle C may be packaged and shipped to hospitals.

The metal component of the femoral hip joint prosthesis P of the present invention is formed of high-strength forged Co-Cr-Mo alloy (ASTM designation F-799) and has its surface polished to a high degree (also known as a color buff finish) to provide for a smoothness having a target surface roughness of four (4) microinches. It has greater fatigue strength, corrosion resistance and wear resistance than stainless steel. Additionally, it resists pitting and crevice corrosion in the body environment.

Referring now to FIG. 3, there is shown the femoral hip joint prosthesis P of the present invention immediately following its implantation in the femur bone 20. As is customary, the femur bone 20 is prepared by reaming the intramedullary canal 21 into which PMMA or other suitable bone cement is introduced under pressure. Promptly after introduction of the bone cement into the canal 21 and before the cement has had an opportunity to set, the femoral hip joint prosthesis P including its preapplied cement mantle C is inserted, distal end first, into the cement with the result that an outer cement mantle 22 is formed around the stem 11 and preapplied cement mantle C. Any excess cement is wiped away leaving an exposed upper end 23. Prior to introduction of cement in the canal, a cement restrictor 28 is positioned therein. As previously mentioned during such insertion, the upper ends 36 of the wings 34 will be biased inwardly thereby centralizing the distal end of the prosthesis P.

Although for purposes of clarity the preapplied cement mantle C and the outer cement mantle 22 are sectioned differently, it should be understood that, following implantation of the hip joint prosthesis P into the cement in the canal 21, the cement of the preapplied cement mantle C and the cement of the outer cement mantle 22 will be merged into an integral unitary cement mantle.

FIG. 4 shows the implanted femoral hip joint prosthesis P after an extended period, say ten years, following implantation. As can be seen there has occurred a small amount of radiological subsidence, on the average of 2 mm, where the stem 11 of the metal component M has subsided within the preapplied cement mantle C which has become joined with the outer cement mantle 22. As may be seen in FIG. 4, such subsidence within the cement mantle results in the tip 12' of the distal end 12 moving closer to the closed end 30. Because of the tapered-stem, collarless design of Co-Cr-Mo alloy having a highly polished surface, the metal portion M of the femoral hip joint prosthesis P of the present invention is permitted to subside within the cement mantle 22 but to do so without disrupting the cement-bone interface.

Referring now to FIGS. 6 and 7, there is shown another embodiment of femoral hip joint prosthesis P'. Under this embodiment there is provided a metal component M' and a preapplied cement mantle C' having an intermittent configuration. The metal component has a stem 111 which is convergently tapered toward a distal end 112 and extending along a first axis of symmetry A' to an area of juncture with a neck portion 113 lying on a second axis of symmetry B'. Extending from the neck portion 113 is a frustoconically-shaped Morse Taper neck 114 to which may be attached a spherically-shaped Morse Taper Head. As in the previous embodiment, no collar is provided in the femoral hip prosthesis, but rather the portion of the prosthesis joining the stem 111 to the neck 113 follows a smooth arcuate contour in area 115 of the included angle between the respective axes of symmetry A' and B'. The portion of the femoral hip prosthesis opposite the smooth arcuate portion 115, namely, that portion on the outside of the angle between the two axes of symmetry A' and B' has an enlarged shoulder 116 in which is formed a dimple or recess 117 for driving the prosthesis into the femur. As in the previous embodiments, the stem 111 is tapered in both directions.

The femoral hip joint prosthesis further includes a preapplied cement mantle C' of PMMA or other commercially available bone cement. Under this embodiment the preapplied cement mantle C' is placed intermittently on the stem 111 and encapsulates only a portion of the stem 111. The preapplied cement mantle C' extends in intermittent fashion from a closed end 120 spaced from the tip 112' of the distal end 112 to a point on the stem 111 near the beginning of such enlarged shoulder 116.

As can be seen in FIGS. 6 and 7, preapplied cement mantle C' has a series of spaced apart longitudinal rib members 130 extending generally parallel to the axis A' and a series of transverse or circumferential rib members 131 extending circumferentially around the stem 111 in spaced apart manner and joining the longitudinal rib members 130. Since the longitudinal rib members 130 are spaced apart from each other, they will cooperate to define a series of interstices 132 through which the surface of the stem 111 will be visible.

Although the preapplied cement mantle C' of this embodiment is shown as having a series of longitudinal rib members 130 and a series of circumferential members 131 defining the interstices 132, it should be understood that the preapplied cement mantle C' may be of any desired pattern and have interstices 132 of any desired pattern therebetween. Thus, for example, the preapplied cement mantle C' could cover a greater portion of the surface of the stem 111 and simply have circular or other shaped interstices or a lesser portion. However, in all instances the preapplied cement mantle C' will extend beyond the distal end 112 but will not contact the tip 112' and will have a closed end 120 spaced from such tip 112'.

As in the previous embodiment, a plurality of wings 134, preferably three or four in number, extend upwardly in a direction away from the closed end 120 and outwardly away from the axis A. The wings 134 extend in cantilever fashion from a lower end 135 integral with the wall of the preapplied cement mantle C' in a location somewhat upwardly from the closed end 120 and generally aligned with the distal end 112 of the metal component M' to an upper end 136 spaced from the wall of the preapplied cement mantle C'. The wings 134 are resilient and their upper ends 136, prior to insertion in a femoral intramedullary canal, are disposed approximately 3 to 5 millimeters (mm) from the wall of the preapplied cement mantle. Thus, the outer extent in which the upper ends 136 of the wings 134 are positioned is such that upon insertion of the prosthesis P' into the prepared intramedullary canal, the upper ends 136 of the wings 134 will contact the interior wall of the prepared intramedullary canal prior to reaching its fully inserted position and will be biased inwardly thereby centralizing the position of the distal end of the prosthesis P' in the intramedullary canal.

Under this embodiment, it will be appreciated that upon insertion of the prosthesis P' in a prepared intramedullary canal having cement deposited therein, the fresh cement will flow into the interstices 132 to make contact with the polished surface of the stem 111 and will also encapsulate the longitudinal and circumferential rib members 130 and 131 to form a unitary mantle around the stem 111. As will be appreciated, a portion of the new cement mantle aligned with the interstices will be thicker than the new cement mantle covering the longitudinal and circumferential rib members 130 and 131. However, as with the previous embodiment, the stem 111 of the metal component M' will be able to subside within the cement mantle, both those portions of the metal stem 111 surface contacted by the longitudinal and circumferential rib portions 130 and 131 of the preapplied cement mantle C' and those portions aligned with the interstices 132 which are contacted by the new cement placed in the intramedullary canal preparatory to insertion of the stem 111 therein. The distal end 112, during such subsidence, moves in the space between the tip 112' and the closed end 120.

Referring now to FIGS. 8 and 9, there is shown another embodiment of femoral hip joint prosthesis P".

Under this embodiment there is provided a metal component M" and a 2-piece preapplied cement mantle C". The metal component has a stem 211 which is convergently tapered toward a distal end 212 and extending along a first axis of symmetry A" to an area of juncture with a neck portion 213 lying on a second axis of symmetry B". Extending from the neck portion 213 is a frustoconically-shaped Morse Taper neck 214 to which may be attached a spherically-shaped Morse Taper Head. As in the previous embodiments, no collar is provided in the femoral hip prosthesis, but rather the portion of the prosthesis joining the stem 211 to the neck 213 follows a smooth arcuate contour in area 215 of the included angle between the respective axes of symmetry A" and B". The portion of the femoral hip prosthesis opposite the smooth arcuate portion 215, namely, that portion on the outside of the angle between the two axes of symmetry A" and B" has an enlarged shoulder 216 in which is formed a dimple or recess 217 for driving the prosthesis into the femur. As in the previous embodiments, the stem 211 is tapered in both directions.

The femoral hip joint prosthesis further includes a 2-piece preapplied cement mantle C" of PMMA or other commercially available bone cement. Under this embodiment the preapplied cement mantle C" includes a first proximal portion 240 and a second distal portion 250. The proximal portion 240 is contoured to follow the shape of that portion of the metal component M" in the area from the vicinity of the enlarged shoulder 216 and smooth arcuate portion 215 toward the distal end 212. The proximal portion has an inner surface 241 contoured to snugly engage the outer surface of the metal component M" in such area, an outer surface 242 substantially parallel to the inner surface 241, a proximal edge 243 and a distal edge 244. The distance between the inner surface 241 and outer surface 242, and therefore the thickness of such proximal portion 240 is approximately two (2) millimeters. The distance between the proximal edge 243 and the distal edge 244 is in the range of three (3) to five (5) centimeters.

The distal portion 250 fits over the distal end 212 of the stem 211 and includes an inner surface 251 and an outer surface 252 spaced apart approximately two (2) millimeters to provide a thickness of that amount. The distal portion extends from an edge 253 to a closed end 254. The portion of the inner surface 251 adjacent the edge 253 snugly engages that portion of the stem 211 adjacent the distal end 212. The distance from the tip 212' of the distal end 212 to the edge 253 is in the range of one (1) to three (3) centimeters. As can be seen from FIGS. 8 and 9, and as in the previous embodiments, the closed end 254 extends beyond and is spaced from tip 212' of the distal end 212 thereby leaving a space into which the tip 212' and adjacent portions of the distal end 212 may move upon subsidence of the stem 211 within the cement mantle.

If desired two or more spaced apart longitudinal rib members (not shown) may be provided extending between and joining together the proximal portion 240 and distal portion 250.

As in the previous embodiments, a plurality of wings 234, preferably three or four in number, extend upwardly in a direction away from the closed end 254 and outwardly away from the axis A". The wings 234 extend in cantilever fashion from a lower end 235 integral with the wall of the distal portion 250 in a location somewhat upwardly from the closed end 254 to an upper end 236 spaced from the outer surface 252. The wings 234 are resilient and their upper ends 236, prior to insertion in a femoral intramedullary canal, are disposed approximately 3 to 5 millimeters (mm) from the outer surface 252. As with the other embodiments, the outer extent in which the upper ends 236 of the wings 234 are positioned is such that upon insertion of the prosthesis P" into the prepared intramedullary canal, the upper ends 236 of the wings 234 will contact the interior wall of the prepared intramedullary canal prior to reaching its fully inserted position and will be biased inwardly thereby centralizing the position of the distal end of the prosthesis P" in the intramedullary canal.

Under this embodiment, it will be appreciated that upon insertion of the prosthesis P" in a prepared intramedullary canal having cement deposited therein, the fresh cement will flow into the space between the proximal portion 240 and distal portion 250 to make contact with the polished surface of the stem 211 and form a unitary mantle around the stem 211. As will be appreciated, a portion of the new cement mantle in the area between the proximal portion 240 and distal portion 250 will be thicker than the new cement mantle covering such portions. However, as with the previous embodiments, the stem 211 of the metal component M" will be able to subside within the cement mantle, both those portions of the metal stem 211 surface contacted by the proximal portion 240 and distal portion 250 and those portions therebetween which are contacted by the new cement placed in the intramedullary canal preparatory to insertion of the prosthesis P'".

The present invention of a femoral hip joint prosthesis, having a highly polished surface, collarless and a tapered stem and having the integral centralizing feature, permits patients to enjoy long lasting and predictable results.

Modifications will be readily apparent to those skilled in the art. Accordingly, the present invention should be limited only by the scope of the claims.

I claim:

1. A femoral hip joint prosthesis for insertion into a prepared intramedullary canal comprising:
   (a) a structural member formed of metal and having an elongated stem extending from a proximal end to a distal end, said stem tapering from larger to progressively smaller cross-sectional sizes from said proximal end to said distal end, said stem having surfaces with a polished finish; and
   (b) a preapplied cement mantle on said surfaces, in direct engagement with said surfaces forming a non-bonded interfacial relationship therewith which permits subsidence of said stem within said preapplied cement mantle, said cement mantle extending beyond the end of said distal end and including an integral centralizer, said centralizer including outwardly extending means engageable with said prepared intramedullary canal and having a closed end defining a pocket, said centralizer closed end being spaced distally from said stem distal end.

2. The femoral hip joint prosthesis according to claim 1, wherein said means engageable with said prepared intramedullary canal includes a plurality of wings extending outwardly in a direction away from said stem and toward said proximal end.

3. The femoral hip joint prosthesis according to claim 1, wherein said preapplied cement mantle extends intermittently in areas in direct engagement with said polished finish surfaces.

4. The femoral hip joint prosthesis according to claim 3, wherein said preapplied cement mantle includes a proximal portion in non-bonded interfacial relationship with said stem surfaces in the area of said proximal end and a distal portion in non-bonded interfacial relationship with said stem surfaces at said distal end.

5. The femoral hip joint prosthesis according to claim 4, wherein said proximal portion of said cement mantle is connected to said distal portion of said cement mantle.

6. The femoral hip joint prosthesis according to claim 4, wherein said proximal portion of said cement mantle is separate from said distal portion of said cement mantle.

7. A femoral hip joint prosthesis for insertion into a prepared intramedullary canal comprising:
   (a) a structural member formed of a cobalt chrome molybdenum alloy and having an elongated stem extending from a proximal end to a distal end, said stem tapering from larger to progressively smaller cross-sectional sizes from said proximal end to said distal end, said stem having surfaces with a polished finish; and
   (b) a preapplied cement mantle on said surfaces, in direct engagement with said surfaces forming a non-bonded interfacial relationship therewith which permits subsidence of said stem within said preapplied cement mantle, said cement mantle extending beyond the end of said distal end and including an integral centralizer, said centralizer including means engageable with said prepared intramedullary canal and having a closed end defining a pocket, said centralizer closed end being spaced from said stem distal end.

8. The femoral hip joint prosthesis according to claim 7, wherein said means engageable with said prepared intramedullary canal includes a plurality of wings extending outwardly in a direction away from said stem and toward said proximal end.

9. The femoral hip joint prosthesis according to claim 7, wherein said preapplied cement mantle extends intermittently in areas in direct engagement with said polished finish surfaces.

10. The femoral hip joint prosthesis according to claim 9, wherein said preapplied cement mantle includes a proximal portion in non-bonded interfacial relationship with said stem surfaces in the area of said proximal end and a distal portion in non-bonded interfacial relationship with said stem surfaces at said distal end.

11. The femoral hip joint prosthesis according to claim 10, wherein said proximal portion of said cement mantle is connected to said distal portion of said cement mantle.

12. The femoral hip joint prosthesis according to claim 10, wherein said proximal portion of said cement mantle is separate from said distal portion of said cement mantle.

* * * * *

UNITED STATES PATENT AND TRADEMARK OFFICE
CERTIFICATE OF CORRECTION

PATENT NO. : 5,314,493
DATED : May 24, 1994
INVENTOR(S) : W. E. MICHAEL MIKHAIL

It is certified that error appears in the above—identified patent and that said Letters Patent is hereby corrected as shown below:

Column 3, line 36 after the numeral "34" insert --are positioned is such that upon insertion of the prosthesis P into the prepared intramedullary canal, the upper ends 36 of the wings 34--.

Signed and Sealed this

Thirteenth Day of September, 1994

Attest:

BRUCE LEHMAN

*Attesting Officer*

*Commissioner of Patents and Trademarks*